United States Patent [19]

Carey et al.

[11] Patent Number: 5,616,278
[45] Date of Patent: *Apr. 1, 1997

[54] INHIBITION OF SCALE AND CORROSION IN AQUEOUS SYSTEMS

[75] Inventors: William S. Carey, Ridley Park; Andrew Solov, Holland; Libardo A. Perez, Morrisville; Donald T. Freese, Glenside, all of Pa.

[73] Assignee: BetzDearborn Inc., Trevose, Pa.

[*] Notice: The term of this patent shall not extend beyond the expiration date of Pat. No. 5,378,372.

[21] Appl. No.: 635,123

[22] Filed: Apr. 19, 1996

Related U.S. Application Data

[63] Continuation-in-part of Ser. No. 534,364, Sep. 27, 1995, which is a continuation-in-part of Ser. No. 106,452, Aug. 13, 1993, abandoned.

[51] Int. Cl.$^6$ ........................................ C02F 5/14
[52] U.S. Cl. ................ 252/180; 252/181; 210/697; 210/698; 210/699; 210/701
[58] Field of Search ........................ 252/180, 181

[56] References Cited

U.S. PATENT DOCUMENTS

| | | | |
|---|---|---|---|
| 3,776,850 | 12/1973 | Pearson et al. | 252/89 |
| 4,654,159 | 3/1987 | Bush et al. | 252/95 |
| 4,659,481 | 4/1987 | Chen | 210/697 |
| 5,062,962 | 11/1991 | Brown et al. | 210/698 |
| 5,116,513 | 5/1992 | Koskan et al. | 210/698 |
| 5,152,902 | 10/1992 | Koskan et al. | 210/698 |
| 5,183,590 | 2/1993 | Carter et al. | 252/392 |
| 5,248,438 | 9/1993 | Perez | 210/698 |
| 5,256,332 | 10/1993 | Kessler | 252/396 |
| 5,378,372 | 1/1995 | Carey et al. | 252/180 |
| 5,378,390 | 1/1995 | Perez et al. | 252/180 |
| 5,437,712 | 8/1995 | Klatskih et al. | 252/180 |
| 5,468,393 | 11/1995 | Zidovec et al. | 252/180 |
| 5,489,666 | 2/1996 | Carey et al. | 252/180 |
| 5,518,629 | 5/1996 | Perez et al. | 252/180 |
| 5,525,257 | 6/1996 | Kleinstuck et al. | 252/180 |

FOREIGN PATENT DOCUMENTS 4166298  6/1992  Japan.

*Primary Examiner*—Ellen M. McAvoy
*Attorney, Agent, or Firm*—Alexander D. Ricci; Richard A. Paikoff

[57] ABSTRACT

A method and compounds for inhibiting the formation of scale, e.g., barium scale, and controlling corrosion is disclosed. The method is particularly effective at inhibiting or preventing corrosion of ferrous-based metals in contact with the aqueous systems such as cooling water systems. The method comprises introducing into the aqueous system a compound of the general formula:

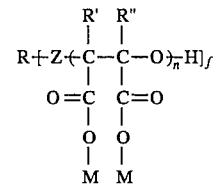

wherein R is hydrogen, alkyl, aryl, substituted alkyl or substituted aryl; R' and R" are each independently hydrogen, $C_{1-4}$ alkyl or $C_{1-4}$ substituted alkyl; Z is O, S, NH or NR, where R is as described above; n is a positive integer greater than 1; f is a positive integer; and M is hydrogen, a water soluble cation (e.g., $NH_4^+$, alkali metal), or a $C_{1-3}$ alkyl group.

15 Claims, No Drawings

INHIBITION OF SCALE AND CORROSION IN AQUEOUS SYSTEMS

This is a continuation-in-part of application Ser. No. 08/534,364 filed Sep. 27, 1995, now pending, which is a continuation-in-part of application Ser. No. 08/106,452 filed Aug. 13, 1993, now abandoned.

FIELD OF THE INVENTION

The present invention relates to the treatment of water to inhibit scale and control corrosion of metals in contact with aqueous systems. More particularly, the present invention relates to the use of a modified polyepoxysuccinic acid to inhibit scale or prevent corrosion of ferrous-based metals in contact with aqueous systems.

BACKGROUND OF THE INVENTION

In industrial cooling systems, water such as from rivers, lakes, ponds, etc., is employed as the cooling media for heat exchangers. The cooling water from heat exchangers is typically passed through a cooling tower, spray pond or evaporative system prior to discharge or reuse. In these systems, the cooling effect is achieved by evaporating a portion of the water passing through the system. Because of the evaporation which takes place during cooling, dissolved materials in the water become concentrated, making the water more corrosive.

In cooling systems, corrosion causes two basic problems. The first and most obvious is the failure of equipment, resulting in replacement costs and plant downtime. Also, decreased plant efficiency occurs due to the loss of heat transfer. The accumulation of corrosion products causes heat exchanger fouling, resulting in the loss of heat transfer.

Ferrous-based metals, e.g., iron metal and metal alloys containing iron (mild steel), are routinely used in the construction of cooling systems due to their low cost and availability. As the system water passes over or through these ferrous-based metal containing devices, they are subjected to corrosion processes. Corrosion inhibitors are generally added as part of a water treatment program in cooling systems to prevent and inhibit the corrosion of ferrous-based metal containing devices.

Chromates, molybdates, zinc, phosphates or polyphosphates, and phosphonates have been used to inhibit the corrosion of ferrous-based metals in contact with the system water of cooling systems. Each treatment, however, presents certain drawbacks. Chromate is highly toxic and presents handling and disposal problems. Phosphates, polyphosphates, and phosphonates contribute to the eutrophication of the receiving water upon discharge, leading to restriction of their discharge by regulatory bodies. The discharge of cooling tower blowdown containing zinc, a heavy metal, is also regulated due to its aquatic toxicity. Molybdate and tungstate are not effective at low concentrations and generally are combined with other conventional inhibitors, such as phosphonates, to be cost effective.

There exists a need, therefore, for a more environmentally acceptable corrosion inhibitor of ferrous-based metals in contact with aqueous systems. In particular, there is a need for a non-phosphorous containing organic corrosion inhibitor.

Preventing the corrosion and scaling of industrial heat transfer equipment is essential to the efficient and economical operation of a cooling water system. Excessive corrosion of metallic surfaces can cause the premature failure of process equipment, necessitating downtime for the replacement or repair of the equipment. Additionally, the buildup of corrosion products on the heat transfer surface reduces efficiency, thereby limiting production or requiring downtime for cleaning.

SUMMARY OF THE INVENTION

The present invention provides an effective method and novel compounds for inhibiting scale and controlling corrosion of metals, particularly ferrous-based metals in contact with aqueous systems.

The method of the present invention comprises treating industrial waters with a modified poly[epoxysuccinic acid] of the general formula:

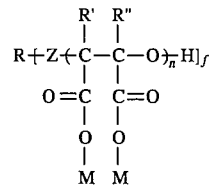

wherein R, when present, is a substituted or non-substituted alkyl or aryl moiety having a carbon chain up to the length where solubility in an aqueous solution is lost, or a repeat unit obtained after polymerization of an ethylenically unsaturated compound; R' and R" each independently are hydrogen, $C_{1-4}$ alkyl or $C_{1-4}$ substituted alkyl; Z is O, S, NH, or NR, where R is as described above; n is a positive integer greater than 1; f is a positive integer; and M is hydrogen, a water soluble cation (e.g., $NH_4^+$, alkali metal), or a non-substituted lower alkyl group having from 1 to 3 carbon atoms. (When R is not present, Z may be $MO_3S$, where M is as described above.)

In a preferred embodiment of the invention, R is a $C_1$-$C_{20}$ alkyl or substituted alkyl moiety, or a $C_4$-$C_9$ aryl or substituted aryl moiety, R' and R" are hydrogen, Z is NH, n is greater than 1, f is 1–2, and M is $Na^+$.

In one particularly preferred embodiment of the invention, R is a —$CH_2C_6H_4CH_2$— moiety, R' and R" are hydrogen, Z is NH, n is greater than 1, f is 2, and M is $Na^+$. In another particularly preferred embodiment of the invention, R is $HOCH_2(CHOH)_3C(CO_2H)$—, R' and R" are hydrogen, Z is —O—, n is greater than 1, f is 1, and M is $Na^+$.

The compositions of the present invention should be added to the aqueous system for which scale control and/or corrosion inhibition activity of the ferrous-based metal parts in contact with an aqueous system is desired, in an amount effective for the purpose. This amount will vary depending upon the particular system for which treatment is desired and will be influenced by factors such as the area subject to corrosion, pH, temperature, water quantity and respective concentrations in the water of corrosive species. For the most part, the present invention will be effective when used at levels of from about 0.025–500 parts per million (ppm) of water, and preferably from about 0.05–100 ppm of water contained in the aqueous system to be treated. The present invention may be added directly to the desired water system in a fixed quantity and in a state of an aqueous solution, continuously or intermittently.

DESCRIPTION OF THE PREFERRED EMBODIMENTS

The present invention pertains to a novel method of inhibiting scale, e.g., barium scale, and controlling corrosion of ferrous-based metals in contact with aqueous systems, e.g., cooling water, steam generating, gas scrubbing and pulp and papermaking systems. Specifically, the method of the present invention comprises adding to an aqueous system a modified poly[epoxysuccinic acid] of the general formula:

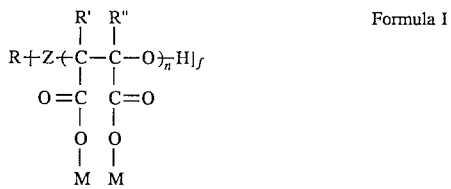

Formula I wherein R is H, a substituted or non-substituted alkyl or aryl moiety having a carbon chain up to the length where solubility in an aqueous solution is lost, or a repeat unit obtained after polymerization of an ethylenically unsaturated compound; R' and R" are hydrogen, $C_{1-4}$ alkyl or $C_{1-4}$ substituted alkyl; Z is O, S, NH, or NR, where R is as described above; n is a positive integer greater than 1; f is a positive integer; and M is hydrogen, a water soluble cation (e.g., $NH_4^+$, alkali metal), or a non-substituted lower alkyl group having from 1 to 3 carbon atoms.

The compounds of the present invention can be prepared by incorporating reagents containing an α-hydroxycarboxylic acid (αHCA) functionality into a poly[epoxysuccinic acid] (PESA) polymer matrix. The αHCA compounds can be obtained by the ring opening reaction of a suitable reagent (R—[—Z—H]f) with a salt or ester of epoxysuccinic acid (ESA). The αHCA compound can be synthesized prior to the incorporation reaction (Scheme A) or be generated in situ by conducting the polymerization of ESA in the presence of a suitable ring-opening reagent (Scheme B).

Scheme A

Step 1:

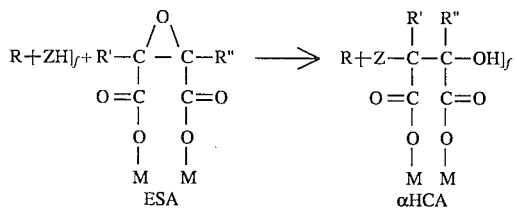

Step 2:

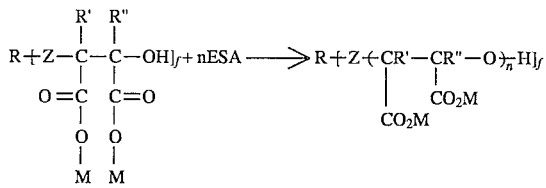

Scheme B

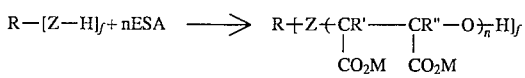

(R, R', R", n, Z, f and M are as described above)

For a general review of ring-opening reactions of epoxides to prepare αHCA compounds, see March, "Advanced Organic Chemistry-Reactions, Mechanisms, and Structures", 2d Edition, Chapter 10, McGraw-Hill, New York, 1977.

Methods for conducting the polymerization of ESA, Scheme A-Step 2 and Scheme B, are described by Pearson et al., U.S. Pat. No. 3,776,850 and Bush et al., U.S. Pat. No. 4,654,159, both incorporated by reference.

The reaction can be performed neat, or in aqueous or non-aqueous solvents. If the resulting product is non-aqueous it should be modified by traditional techniques known to those skilled in the art to yield a water soluble product (e.g., hydrolysis of ester derivatives).

In a preferred embodiment of the invention, aqueous solutions of the compounds of the present invention are prepared by reacting an amine with an aqueous solution of disodium epoxysuccinate ($ESA.Na_2$) in the presence of calcium hydroxide.

The reaction is typically conducted under atmospheric conditions at about 30° C.–100° C., preferably from 80° C. to 100° C. The molar ratio of the ring opening reagent R-[Z—H]f to $ESA.Na_2$, relative to functionality (f) may fall within the range of about 1:2 to 1:1000, with a range of 1:5 to 1:100 being preferred. The molar ratio of calcium hydroxide to $ESA.Na_2$ or $ESA.Na_2$+αHCA may fall within the range of 1:20 to 1:3, with a ratio of 1:10 being preferred.

It will be appreciated that certain by-products (e.g., disodium tartrate, PESA, and αHCA compounds) may be produced along with the compounds of the present invention in the course of the above reaction schemes. The desired reaction products can be readily recovered from the reaction product by known methods; however, it is feasible and economical to employ the compounds of the present invention as produced without separation or purification.

The treatment levels of compound added to an aqueous system can range from about 0.025 to 500 parts per million of water, and preferably from about 0.05 to 100 parts per million of water contained in the aqueous system to be treated. The concentration of compound necessary to provide effective scale control and corrosion inhibition will, of course, vary from system to system. The treatment level will vary, in part, with changes in temperatures and pH, water quantity and respective concentrations in the water of corrosive species.

The compounds may be added directly into the desired water system in a fixed quantity and in a state of an aqueous solution, continuously or intermittently. As noted, the compounds of the present invention are expected to exhibit scale inhibition, e.g., calcium carbonate, barium sulfate, calcium oxalate, calcium sulfate and silica/silicate activity. In addition, the compounds of the present invention may also be used with topping agent components in order to enhance the scale controlling and corrosion inhibition properties thereof. Such topping components are readily known to those skilled in the art. Details of such compounds are disclosed by Chen, U.S. Pat. No. 4,659,481, incorporated herein by reference. It is expected that the compounds of the present invention may be used in conjunction with the polymers and topping components of Chen '481 to provide treatment programs which effectively inhibit corrosion and scale deposition in water systems.

Suitable topping agents include polyacrylates, phosphoric acid and water soluble salts thereof, phosphonic acids and water soluble salts thereof, polyvalent metal salts, azole compounds, molybdate and tungstate compounds and mixtures thereof.

A suitable polyacrylate is represented by the following formula:

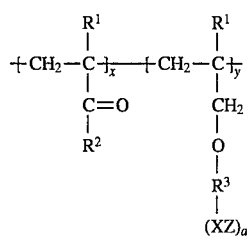

wherein $R^1$ is H or lower alkyl ($C_1$-$C_3$); $R^2$ is OH, OM or $NH_2$; M is a water soluble cation; $R^3$ is a hydroxy substituted alkyl or alkylene radical having from 1 to 6 carbon atoms or a non-substituted alkyl or alkylene radical having from 1 to 6 carbon atoms; X, when present, is an anionic radical selected from $SO_3$, $PO_3$, $PO_4$ and $CO_2$; Z, when present, is H or any water soluble cation or cations which together counterbalance the valence of the anionic radical; a is 0 or 1, the molar ratio of x:y of the polymer being between 30:1 and 1:20.

The phosphoric acid may be orthophosphoric acid or pyrophosphoric acid or a water soluble salt thereof. The phosphonic acid may be 1-hydroxyethane-1, 1-diphosphonic acid, 2-phosphonobutane-1,2,4-tricarboxylic acid or hydroxyphosphonoacetic acid. The polyvalent metals may be $Zn^{2+}$, $Mn^{2+}$ or $Sn^{2+}$. The azole compound may be 1,2,3-tolyltriazole, benzotriazole or butylbenzotriazole. The molybdate compound may be sodium molybdate or potassium molybdate. The tungstate compound may be sodium or potassium tungstate.

The topping agents may be added to the system in an amount of about 0.01 to 500 ppm of said system.

The invention will now be further described with reference to a number of specific examples which are to be regarded solely as illustrative and not as restricting the scope of the present invention.

EXAMPLE I

Preparation of aspartic acid, 3-hydroxy, N-[2-ethane sulfonic acid]-trisodium salt via Reaction Scheme A, Step 1.

A suitable reaction flask was equipped with a magnetic stirrer, reflux condenser, nitrogen sparge, thermometer, and addition ports. Taurine (99%, 12.64 g, 0.1 mole) and 67 ml of deionized water were charged to the flask and sparged with nitrogen. Aqueous sodium hydroxide (50%, 8 g, 0.1 mole) was then charged to the flask to yield a clear, colorless liquid followed by $ESA.Na_2$ (90%, 20.54 g, 0.105 mole) being charged to the flask. The resulting slurry was heated at 90°±2° C. for 16.5 hours under a nitrogen atmosphere. The resulting clear solution was isolated and diluted to 130 g with deionized water.

The structure of the resulting aspartic acid, 3-hydroxy, N-[2-ethanesulfonic acid]-trisodium salt, example reference αHCA(8), was confirmed by $^{13}C$ NMR spectroscopy. The product yield was estimated to be 93.3 mole % via integration of the methine carbons of the $^{13}C$ NMR spectrum.

EXAMPLE II

Preparation of poly[oxy(1,2-dicarboxylic acid-1,2-ethanediyl)]α-hydroxy-ω-[(ethanesulfonic acid)2-amino]-sodium salt via Reaction Scheme A, Step 2.

To a reactor setup similar to that described in Example I was charged aqueous aspartic acid, 3-hydroxy, N-[2-ethane sulfonic acid]-trisodium salt (29.2%, 11.07 g, 0.01 mole), 48 ml deionized water, and $ESA.Na_2$ (90%, 37.16 g, 0.19 mole). The solution was sparged with nitrogen and adjusted to a pH of 10.8 with aqueous sodium hydroxide (50%). Calcium hydroxide (98%, 1.51 g, 0.02 mole) slurried in 20 ml of deionized water was then charged to the flask and the mixture was heated to 80°±2° C. for 15.5 hours. The resulting solution was then filtered, diluted to 130 g with deionized water, and collected.

The structure of the product, example reference 10, was verified by $^{13}C$ NMR spectroscopy. Residual 3-hydroxy, N-[2-ethanesulfonic acid]-trisodium salt was also detected. Approximately 23.4 mole % of the $ESA.Na_2$ hydrolyzed to disodium tartrate under these reaction conditions.

EXAMPLE III

Preparation of poly[oxy(1,2-dicarboxylic acid-1,2-ethanediyl)]α-hydro-ω-[(ethanesulfonic acid)2-amino]-sodium salt via Reaction Scheme B.

To a reactor similar to that described in Example I was charged $ESA.Na_2$ (90%, 19.56 g, 0.1 mole), 27 ml deionized water, and taurine (99%, 0.63 g, 0.005 mole). The solution was sparged with nitrogen and adjusted to a pH of 10.1 with aqueous sodium hydroxide (50%). Calcium hydroxide (98%, 0.76 g, 0.01 mole) slurried in 10 ml of deionized water was then charged to the flask and the mixture was heated to 80°±2° C. for 17 hours. The resulting solution was then filtered, diluted to 65 g with deionized water, and collected.

The $^{13}C$ NMR of the product, example reference 9, was similar to that of Example II. No residual taurine was detected. Approximately 22.2 mole % of the $ESA.Na_2$ hydrolyzed to the disodium tartrate by-product under these reaction conditions.

Using the above-described preparative techniques, several other modified PESA analogs were prepared. The final products were typically a mixture of the modified PESA analog, residual αHCA, and unmodified PESA (collectively considered the "actives" portion in testing), and sodium tartrate by-product. The results of these preparations are set forth in Table I. Several αHCA analogs (Formula I, n=1) were also prepared for evaluation. These compounds are also listed in Table I for reference.

TABLE I

Modified PESA Synthesis Summary[a]

$$R + Z + CR' \underset{|}{\phantom{x}} CR'' \underset{|}{\phantom{x}} O \rightarrow_n H]_f$$
$$CO_2M \quad CO_2M$$

R' = R'' = H, M = Na, n > 1

| Sample | Mole Ratio $ESA.Na_2$:R+Z—H]$_f$ | Composition[b] Wt. % Actives: Wt. % $TA.Na_2$ |
|---|---|---|
| | R = $C_4H_9$—, Z = —NH—, f = 1 | |
| αHCA[c](1) 1 | 1.0:1.0 20.0:1.0 | 79:21 |
| | R = $C_4H_9$—, Z = —O—, f = 1 | |
| αHCA(2) 2 | 1.0:1.0 6.7:1.0 | 85:15 |
| | R = $C_6H_{13}$—, Z = —NH—, f = 1 | |

TABLE I-continued

Modified PESA Synthesis Summary[a]

$$R + Z + CR' - CR'' - O \}_n H]_f$$
$$\phantom{R + Z + }| \phantom{- CR'' -} |$$
$$\phantom{R + Z + }CO_2M \phantom{-} CO_2M$$

$R' = R'' = H, M = Na, n > 1$

| Sample | Mole Ratio $ESA.Na_2 : R + Z - H]_f$ | Composition[b] Wt. % Actives: Wt. % TA.Na$_2$ |
|---|---|---|
| αHCA(3) | 1.0:1.0 | |
| 3 | 20.0:1.0 | 72:28 |
| $R = C_6H_5 - CH_2 -, Z = -NH-, f = 1$ | | |
| αHCA(4) | 1.0:1.0 | |
| 4 | 20.0:1.0 | 81:19 |
| $R = C_6H_5 - CH_2 -, Z = -S-, f = 1$ | | |
| αHCA(5) | 1.0:1.0 | |
| 5 | 10.0:1.0 | 83:17 |
| $R = (HOCH_2 - CH_2)_2 -, Z = N-, f = 1$ | | |
| αHCA(6) | 1.0:1.0 | |
| 6 | 6.7:1.0 | 84:16 |
| $R = (HOCH_2)_3C-, Z = -NH-, f = 1$ | | |
| αHCA(7) | 1.0:1.0 | |
| 7 | 10.0:1.0 | 81:19 |
| $Z = NaO_3S-$ | | |
| 8 | 20.0:1.0 | 86:14 |
| $R = NaO_3S - CH_2CH_2 -, Z = -NH-, f = 1$ | | |
| αHCA(8) | 1.0:1.0 | |
| 9 | 20.0:1.0 | 78:22 |
| 10 | 20.0:1.0 | 76:24 |
| $R = HOCH_2(CHOH)_3C(CO_2H) -, Z = -O-, f = 1$ | | |
| 11 | 10.0:1.0 | 80:20 |
| $R = -C(CO_2H)(CHOH)_2 - C(CO_2H) -, Z = -O-, f = 2$ | | |
| 12 | 20.0:1.0 | 78:22 |
| $R = -(C_6H_{12}) -, Z = -NH-, f = 2$ | | |
| αHCA(9) | 1.0:1.0 | |
| 13 | 20.0:1.0 | 80:20 |
| $R = meta-CH_2 - C_6H_4 - CH_2 -, Z = -NH-, f = 2$ | | |
| αHCA(10) | 1.0:1.0 | |
| 14 | 10.0:1.0 | 83:17 |
| $R = para-CH_2 - C_6H_4 - CH_2 -, Z = -NH-, f = 2$ | | |
| αHCA(11) | 1.0:1.0 | |
| 15 | 10.0:1.0 | 79:21 |
| $R = para-CH_2 - C_6H_4 - CH_2 -, Z = -S-, f = 2$ | | |
| αHCA(12) | 1.0:1.0 | |
| 16 | 6.7:1.0 | 87:13 |

[a]Mole ratio of $Ca(OH)_2:ESA.Na_2 + \alpha HCA$ (Scheme A) or $ESA.Na_2$ (Scheme B) was 1:10 for all reactions.
[b]Reported as a weight percent of the organic solid content of the product; $TA.Na_2$ stands for disodium tartrate
[c]Corresponding αHCA analog, n = 1

Table II summarizes the static barium sulfate scale inhibition testing of the polymers of the present invention compared to hexametaphosphate, a known prior art barium sulfate scale inhibitor. The tests were conducted in duplicate by adding the treatment to a solution containing $Ba^{2+}$ and $SO_4^{2-}$. After heating, the solutions were filtered through a 0.2 μm filter membrane, and the filtrate analyzed for $Ba^{2+}$ by inductively coupled plasma atomic emission spectroscopy (ICP). The average percent inhibition was calculated from the $Ba^{2+}$ concentration measurements of the treated, stock and control solutions. As shown in Table II, the modified PESA compounds are comparable in activity to the hexametaphosphate.

TABLE II

Barium Sulfate Scale % Inhibition

Conditions: 2 ppm $Ba^{2+}$, 1000 ppm $SO_4^{2-}$
Stock Solution pH = 5.5
Temperature = 60° C.
Duration = 1 hour

| Sample | 1 ppm Actives | 2 ppm Actives |
|---|---|---|
| Hexametaphosphate | 97 | 94 |
| 2 | 100 | 100 |
| 7 | 100 | 100 |
| 8 | 100 | 100 |
| 9 | 100 | 100 |
| 11 | 99 | 97 |
| 12 | 98 | 97 |
| 14 | 100 | 100 |

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method for controlling the formation and deposition of scale forming salts including barium scale in an aqueous system comprising introducing into said aqueous system a sufficient amount for the purpose of a treatment comprising a compound of the general formula:

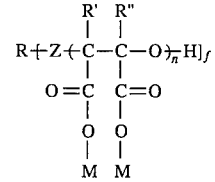

wherein R is alkyl, $C_4$-$C_9$ aryl, substituted alkyl or $C_4$-$C_9$ substituted aryl; R' and R" are each independently hydrogen, $C_{1-4}$ alkyl or $C_{1-4}$ substituted alkyl; Z is NH, NR, O or S; n is a positive integer greater than 1; f is a positive integer; and M is H, a water soluble cation or a $C_{1-3}$ alkyl group.

2. The method as recited in claim 1 further comprising adding to said aqueous system a sufficient amount for the purpose of a topping agent selected from the group consisting of polyacrylates, phosphoric acids and water soluble salts thereof, phosphonic acids and water soluble salts thereof, polyvalent metal salts and azole compounds.

3. The method as recited in claim 2 wherein said polyacrylate has the formula:

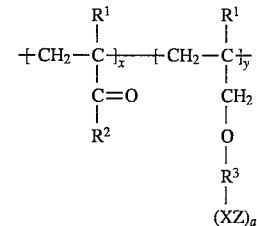

wherein each $R^1$ is independently H or lower alkyl; $R^2$ is OH, $NH_2$ or OM; M is a water soluble cation; $R^3$ is a hydroxy substituted alkyl or alkylene radical having from about 1 to 6 carbon atoms; X is $SO_3$, $PO_3$, $PO_4$ and $CO_2$; Z is H or a water soluble cation or cations; and a is 0 or 1.

4. The method as recited in claim 3 wherein said aqueous system is a cooling water system.

5. The method as recited in claim 4 wherein R is $C_1$-$C_{20}$ alkyl.

6. The method as recited in claim 4 wherein R is $C_4$-$C_6$ aryl.

7. The method as recited in claim 4 wherein R is —$CH_2C_6H_4CH_2$— and f is 2.

8. The method as recited in claim 1 wherein M is $Na^+$.

9. The method as recited in claim 4 wherein said compound is added to the aqueous system at active treatment levels ranging from about 0.025 to about 500 parts per million.

10. The method as recited in claim 9 wherein said compound is added to the aqueous system at active treatment levels ranging from about 0.05 to about 100 parts per million.

11. The method as recited in claim 4 wherein the molar ratio of x:y is from about 30:1 to 1:20.

12. The method as recited in claim 3 wherein said aqueous system is a steam generating system.

13. The method as recited in claim 3 wherein said aqueous system is a gas scrubbing system.

14. The method as recited in claim 3 wherein said aqueous system is a pulp and papermaking system.

15. The method as recited in claim 1 when said barium scale comprises barium sulfate scale.

* * * * *